(12) United States Patent
Freasier et al.

(10) Patent No.: US 12,070,532 B2
(45) Date of Patent: Aug. 27, 2024

(54) NITRIC OXIDE AND CHLORHEXIDINE RELEASING CATHETER FOR ANTI-PLATELET AND ANTIMICROBIAL DUAL FUNCTIONALITY

(71) Applicant: Becton, Dickinson and Company, Franklin Lakes, NJ (US)

(72) Inventors: James Freasier, Salt Lake City, UT (US); Brendan Laine, Salt Lake City, UT (US); Gidon Ofek, Millcreek, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/093,451

(22) Filed: Nov. 9, 2020

(65) Prior Publication Data
US 2021/0146014 A1    May 20, 2021

Related U.S. Application Data

(60) Provisional application No. 62/936,935, filed on Nov. 18, 2019.

(51) Int. Cl.
*A61L 29/08*    (2006.01)
*A61L 29/04*    (2006.01)

(52) U.S. Cl.
CPC ........... *A61L 29/085* (2013.01); *A61L 29/049* (2013.01); *A61L 2300/114* (2013.01); *A61L 2300/404* (2013.01); *A61L 2300/42* (2013.01)

(58) Field of Classification Search
CPC ........ B05B 13/02; A61L 29/08; A61L 29/085; A61L 27/54; A61K 31/21; A61M 25/104
See application file for complete search history.

(56) References Cited

U.S. PATENT DOCUMENTS 5,772,640 A    6/1998   Modak et al.
6,083,208 A    7/2000   Modak et al.
(Continued)

FOREIGN PATENT DOCUMENTS

AT    245039 T    8/2003
AU    730158 B2    3/2001
(Continued)

OTHER PUBLICATIONS

E1, Tecoflex TPU, Lubrizol, 2022, pp. 1-4 (Year: 2022).*
E2, Tecothane TPU, Lubrizol, 2022, pp. 1-3 (Year: 2022).*

*Primary Examiner* — Robert S Walters, Jr.
*Assistant Examiner* — Andrew J Bowman
(74) *Attorney, Agent, or Firm* — Kirton McConkie; Whitney Blair; Kevin Stinger

(57) ABSTRACT

A catheter configured to release nitric oxide and chlorhexidine providing anti-platelet and antimicrobial properties is manufactured by impregnating a thermoplastic polyurethane catheter extrusion with a nitric oxide releasing compound and with chlorhexidine. Thereafter, the impregnated catheter extrusion is coated with a polyurethane coating comprising chlorhexidine and/or a nitric oxide releasing compound. In the impregnating step, the catheter extrusion may be exposed to a solvent having the nitric oxide releasing compound and chlorhexidine dissolved therein. The solvent is removed from the catheter extrusion. In the coating step, the impregnated catheter extrusion may be dip coated in a polymer solution comprising polyurethane and chlorhexidine and/or a nitric oxide releasing compound in a suitable solvent. The nitric oxide releasing compound, impregnated and/or coated, may be selected from s-nitroso-n-acetylpenicillamine (SNAP), s-nitrosoglutathione (GSNO), and mixtures thereof. The chlorhexidine, impregnated and/or coated, (Continued)

may be selected from chlorhexidine diacetate, chlorhexidine base, chlorhexidine gluconate, and mixtures thereof.

14 Claims, 1 Drawing Sheet

(56) References Cited

U.S. PATENT DOCUMENTS

| | | | |
|---|---|---|---|
| 6,106,505 | A | 8/2000 | Modak et al. |
| 6,626,873 | B1 | 9/2003 | Modak et al. |
| 2001/0024661 | A1 | 9/2001 | Modak et al. |
| 2002/0094985 | A1 | 7/2002 | Herrmann et al. |
| 2004/0039349 | A1 | 2/2004 | Modak et al. |
| 2004/0171589 | A1* | 9/2004 | Herrmann ............... A61K 31/53 514/509 |
| 2004/0208908 | A1* | 10/2004 | Modak .................... A61L 27/54 424/618 |
| 2005/0158449 | A1* | 7/2005 | Chappa ................. B05B 7/0861 118/305 |
| 2010/0233288 | A1 | 9/2010 | Gupta et al. |
| 2012/0052185 | A1 | 3/2012 | Gupta et al. |
| 2012/0277783 | A1* | 11/2012 | Cummins ........... A61M 25/104 606/191 |
| 2014/0124125 | A1 | 5/2014 | Nussbaum et al. |
| 2014/0314818 | A1* | 10/2014 | Giare-Patel ............. A61L 29/16 514/635 |
| 2015/0366831 | A1 | 12/2015 | Brisbois et al. |
| 2016/0331871 | A1 | 11/2016 | Gupta et al. |
| 2017/0028106 | A1 | 2/2017 | Brisbois et al. |
| 2020/0171211 | A1 | 6/2020 | Giare-Patel et al. |

FOREIGN PATENT DOCUMENTS

| | | | |
|---|---|---|---|
| CA | 2241461 | A1 | 7/1997 |
| CA | 2855218 | A1 | 5/2013 |
| CA | 3021799 | A1 | 5/2013 |
| CA | 2899477 | A1 | 8/2014 |
| CN | 1282216 | A | 1/2001 |
| CN | 102056600 | A | 5/2011 |
| CN | 105307695 | A | 2/2016 |
| CN | 106456785 | A | 2/2017 |
| DE | 69629128 | T2 | 6/2004 |
| EP | 0874655 | A1 | 11/1998 |
| EP | 1273313 | A2 | 1/2003 |
| EP | 2416731 | A1 | 2/2012 |
| EP | 2754413 | A1 | 7/2014 |
| EP | 2780051 | A1 | 9/2014 |
| EP | 2953660 | A2 | 12/2015 |
| EP | 3102240 | A1 | 12/2016 |
| EP | 3673928 | A1 | 7/2020 |
| ES | 2530731 | T3 | 3/2015 |
| ES | 2705747 | T3 | 3/2019 |
| HK | 1220643 | A1 | 5/2017 |
| JP | 2000507842 | A | 6/2000 |
| JP | 2012520126 | A | 9/2012 |
| JP | 2016514171 | A | 5/2016 |
| JP | 2019093208 | A | 6/2019 |
| JP | 6763988 | B2 | 9/2020 |
| WO | 9725085 | A1 | 7/1997 |
| WO | WO2010/104760 | * | 2/2010 ........... A61L 29/085 |
| WO | 2013070951 | A | 5/2013 |
| WO | 2014124125 | A2 | 8/2014 |
| WO | 2015119678 | A1 | 8/2015 |

* cited by examiner

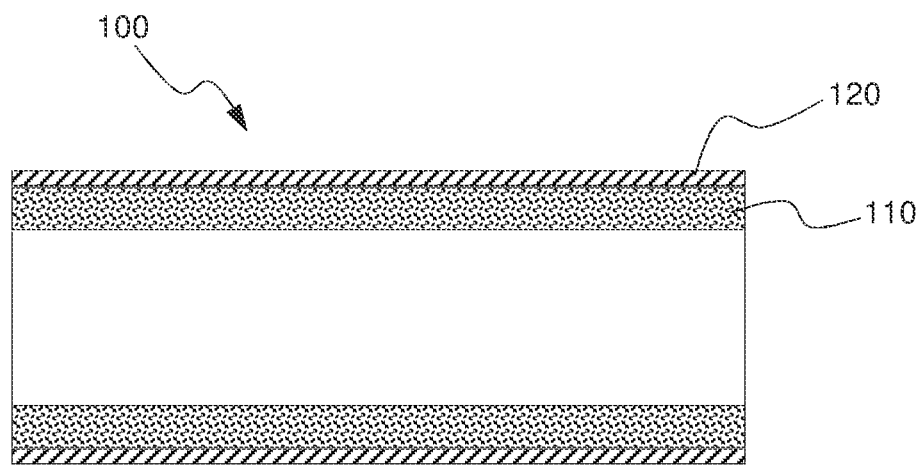

NITRIC OXIDE AND CHLORHEXIDINE RELEASING CATHETER FOR ANTI-PLATELET AND ANTIMICROBIAL DUAL FUNCTIONALITY

RELATED APPLICATIONS

This application claims the benefit of U.S. Provisional Patent Application No. 62/936,935, filed Nov. 18, 2019, and entitled NITRIC OXIDE AND CHLORHEXIDINE RELEASING CATHETER FOR ANTI-PLATELET AND ANTIMICROBIAL DUAL FUNCTIONALITY, which is incorporated herein in its entirety.

BACKGROUND

The present disclosure relates to a catheter impregnated and coated with nitric oxide (NO) releasing compound(s) and chlorhexidine to provide dual anti-platelet and antimicrobial functionality.

Catheters are commonly used for a variety of infusion therapies. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses. For example, catheters are used for infusing fluids, such as normal saline solution, various medicaments, and total parenteral nutrition into a patient, withdrawing blood from a patient, as well as monitoring various parameters of the patient's vascular system.

Catheters are commonly introduced into the vasculature of a patient as part of an intravenous catheter assembly. The catheter assembly generally includes a catheter hub, which supports the catheter, the catheter hub being coupled to a needle hub which supports an introducer needle. The introducer needle is extended and positioned within the catheter such that a beveled portion of the needle is exposed beyond a tip of the catheter. The beveled portion of the needle is used to pierce the skin of the patient to provide an opening whereby to insert the needle in the vasculature of the patient. Following insertion and placement of the catheter, the introducer needle is removed from the catheter thereby providing intravenous access to the patient.

Catheter-related bloodstream infections (CRBSIs) are caused by the colonization of microorganisms in patients with intravascular catheters and I.V. access devices. These infections are an important cause of illness and excess medical costs, as approximately 250,000-400,000 cases of central venous catheter (CVC) associated bloodstream infections occur annually in US hospitals. In addition to the monetary costs, these infections are associated with anywhere from 20,000 to 100,000 deaths each year. Despite guidelines to help reduce healthcare associated infections (HAIs), catheter-related bloodstream infections continue to plague our healthcare system.

Impregnating catheters with various antimicrobial agents is one approach that has been implemented to prevent these infections. These catheters, however, have given less than satisfactory results. In addition, some microbes have developed resistance to the various antimicrobial agents in the system.

When catheters, or other biomedical devices, contact blood for a prolonged period, plasma proteins, such as Factor XII and Factor XI, are activated and adhere to the device surface. In addition to thrombus formation, biofilm formation and bacterial infection can occur.

State of the art anti-platelet/anti-thrombogenic technologies generally employ surface modification techniques to delay protein adhesion or heparin based technologies.

State-of-the-art anti-platelet and anti-thrombogenic technologies are generally ineffective for long periods of time (greater than 7 days in blood stream) since they try to prevent protein adhesion, which is a complicated phenomenon that generally overcomes all surface modification techniques. While heparin technologies are more successful, however, they are extremely expensive and difficult for scale-up in rapid throughput manufacturing scenarios.

Accordingly, there is a need in the art for catheters having improved antimicrobial and anti-platelet capabilities. Such method and systems are disclosed herein.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure has been developed in response to problems and needs in the art that have not yet been fully resolved by currently available antimicrobial and anti-platelet catheters. The disclosed catheters provide improved antimicrobial and anti-platelet capabilities by releasing nitric oxide and chlorhexidine. The released nitric oxide in combination with other antimicrobials enhances the overall antimicrobial effects and imparts biofilm penetration and eradication mechanisms.

The present disclosure relates to a method of manufacturing a catheter configured to release nitric oxide and chlorhexidine to provide anti-platelet and antimicrobial properties. The disclosed method uses a multi-step process to apply NO-releasing compound(s) and chlorhexidine to thermoplastic polyurethane catheter extrusions. First, the extrusion is impregnated with the NO-releasing compound(s) and chlorhexidine dissolved in a solvent system. The solvent is evaporated off of the extrusion. The impregnated catheter extrusion is then dip-coated with additional chlorhexidine and/or NO-releasing compound(s) inside of a matrix of polyurethane.

The resulting catheter elutes NO and chlorhexidine simultaneously over a period of time. The elution rate is affected by the concentration of active agents impregnated in and coated on the catheter. It is further affected by properties of the polyurethane in the dip-coating. These properties—molecular weight, coating thickness, and copolymer hard/soft segment ratios and chemistries—affect release kinetics of the active agents and maintain antimicrobial/anti-platelet activity over an extended period of time.

The disclosed catheter is manufactured by first impregnating a thermoplastic polyurethane catheter extrusion with a nitric oxide releasing compound and with chlorhexidine. Thereafter, the impregnated catheter extrusion is coated with a polyurethane coating comprising chlorhexidine and/or a nitric oxide releasing compound.

The impregnating step may be accomplished in one step by exposing the catheter extrusion to a solvent having the nitric oxide releasing compound and chlorhexidine dissolved therein. The catheter extrusion is exposed to the solvent solution for sufficient time to permit the nitric oxide releasing compound and chlorhexidine to penetrate the catheter extrusion. The impregnating step may be accomplished in two steps by exposing the catheter extrusion a solvent having the nitric oxide releasing compound dissolved therein and to a solvent having the chlorhexidine dissolved therein. The catheter extrusion is exposed to the solvent solutions for sufficient time to permit the nitric oxide releasing compound and chlorhexidine to penetrate the catheter extrusion. The impregnating step may occur at room temperature. The impregnating step may occur at a temperature in the range from about 25 to 55° C.

Any physiologically compatible nitric oxide releasing compound may be used. Non-limiting examples of nitric oxide releasing compounds include s-nitroso-n-acetylpenicillamine (SNAP), s-nitrosoglutathione (GSNO), and mixtures thereof.

Non-limiting examples of chlorhexidine include chlorhexidine diacetate, chlorhexidine base, chlorhexidine gluconate, and mixtures thereof.

Any solvent that is compatible with the polyurethane catheter extrusion may be used. The solvent may include methanol. The solvent may include acetone. The solvent may include methyl ethyl ketone (MEK). The solvent may include a mixture of solvents. The solvent may include methanol, acetone, and MEK.

The coating step may be accomplished by dip coating the impregnated catheter extrusion in a polymer solution comprising polyurethane and chlorhexidine and/or a nitric oxide releasing compound in a suitable solvent. The polyurethane in the dip coating polymer solution may comprise an aliphatic polyurethane. The polyurethane in the dip coating polymer solution may comprise an aromatic polyurethane.

The chlorhexidine in the polymer solution may comprise chlorhexidine base. The chlorhexidine concentration in the dip-coating solution may range from 0.5 wt. % to 20 wt. %.

The nitric oxide releasing compound in the polymer solution may be any physiologically compatible nitric oxide releasing compound. Non-limiting examples of nitric oxide releasing compounds include s-nitroso-n-acetylpenicillamine (SNAP), s-nitrosoglutathione (GSNO), and mixtures thereof. The s-nitroso-n-acetylpenicillamine (SNAP) may have a concentration in the solvent from 1 to 20 wt./vol. %.

The solvent for the dip coating polymer solution may comprise methanol, dioxolane, and mixtures thereof. In a non-limiting embodiment, the solvent comprises from 10 vol. % to 25 vol. %, methanol and from 75 vol. % to 90 vol. % dioxolane.

The resulting catheter manufactured as described above is configured to release nitric oxide and chlorhexidine to provide anti-platelet and antimicrobial properties. The catheter includes an extruded thermoplastic polyurethane catheter body impregnated with a nitric oxide releasing compound and with chlorhexidine. The catheter further includes a polyurethane coating on the polyurethane catheter body comprising chlorhexidine. The polymer coating may further comprise a nitric oxide releasing compound.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1 is cross-sectional representation of portion of a catheter body fabricated to contain a nitric oxide (NO) releasing compound and chlorhexidine to provide dual anti-platelet and antimicrobial functionality.

DESCRIPTION OF EMBODIMENTS

The disclosure relates to a catheter impregnated and coated with nitric oxide (NO) releasing compound(s) and chlorhexidine. The combination of nitric oxide and chlorhexidine provides a dual anti-platelet and antimicrobial functionality. Furthermore, nitric oxide in combination with other antimicrobials enhances the overall antimicrobial effects and imparts biofilm penetration and eradication mechanisms. The disclosure further relates to methods of manufacturing a catheter configured to release nitric oxide and chlorhexidine to provide anti-platelet and antimicrobial properties.

Nitric oxide (NO) is a natural platelet activation inhibitor produced by endothelial cells within the body, which also exhibits antimicrobial and biofilm eradication abilities. Nitric oxide is produced by a Nitric Oxide Synthase in endothelial, neural, and other cells within the human body.

NO mediates platelet activation through the soluble guanylate cylase (sGC) pathway: NO binds to the heme iron moeity of sGC, increasing intracellular concentrations of cyclic guanosine monophosphate, which increases concentrations of cyclic adenosine monophasphate, and eventually decreases concentrations of calcium ions—a prominent component of the coagulation responses.

Ultimately, NO activated sGC leads to calcium ion concentration decrease. Additionally, it inhibits phosphoinositide 3-kinase, reduces affinity of platelets towards fibrinogen, and reduces number of fibrinogen binding sites on surface of platelets.

As an antimicrobial agent, NO reacts with physiological concentrations of superoxide to create peroxynitrite which induces oxidative stress, nitrosates amino acids of bacterial cells, oxidizes and breaks their DNA strands, and causes cell membrane damage via lipid peroxidation. Additionally, NO reacts with oxidators to form $N_2O_3$ which reacts with sulfhydryl groups of cysteine residues on bacteria membrane proteins and alters or inhibits their functionality.

An important aspect of the present disclosure is incorporating both a nitric oxide releasing compound and chlorhexidine into a thermoplastic polyurethane catheter extrusion.

By incorporating a nitric oxide releasing compound into the catheter device, the NO releasing compound will degrade over time and release NO in the gaseous phase at physiologically relevant levels to exert the above described physiological mechanisms on the blood stream or infecting bacteria.

The disclosed catheter configured to release nitric oxide and chlorhexidine to provide anti-platelet and antimicrobial properties is manufactured by first impregnating a thermoplastic polyurethane catheter extrusion with a nitric oxide releasing compound and with chlorhexidine. Thereafter, the impregnated catheter extrusion is coated with a polyurethane coating comprising chlorhexidine and/or a nitric oxide releasing compound.

The impregnating step may be accomplished in one step by exposing the catheter extrusion to a solvent having the nitric oxide releasing compound and chlorhexidine dissolved therein. The catheter extrusion is exposed to the solvent solution for sufficient time to permit the nitric oxide releasing compound and chlorhexidine to penetrate the catheter extrusion. The impregnating step may be accomplished in two steps by exposing the catheter extrusion a solvent having the nitric oxide releasing compound dissolved therein and to another solvent having the chlorhexidine dissolved therein. The catheter extrusion is exposed to each of the solvent solutions for sufficient time to permit the nitric oxide releasing compound and chlorhexidine to penetrate the catheter extrusion. The exposure time may range from about 25 minutes to about 240 minutes. The sufficient exposure time is inversely related to the concentration of the nitric oxide releasing compound and chlorhexidine in the solvent. The solvent is then removed from the catheter extrusion by evaporation.

Any physiologically compatible nitric oxide releasing compound may be used. Non-limiting examples of nitric oxide releasing compounds include s-nitroso-n-acetylpenicillamine (SNAP), s-nitrosoglutathione (GSNO), and mixtures thereof. The s-nitroso-n-acetylpenicillamine (SNAP) may have a concentration in the solvent from 0 to 20 wt./vol. %. The s-nitrosoglutathione (GSNO) may have a concentration in the solvent from 0 to 20 wt./vol. %. The combination of SNAP and GSNO must have a concentration in the solvent greater than 0 wt./vol. %.

Chlorhexidine is characterized as being a strong base with cationic properties. It is commercially available in both the free base and stable salt forms. Non-limiting examples of chlorhexidine include chlorhexidine diacetate, chlorhexidine base, chlorhexidine gluconate, and mixtures thereof. The chlorhexidine diacetate may have a concentration in the solvent from 0.5 to 6.5 wt./vol. %. The chlorhexidine base may have a concentration in the solvent from 0 to 2.5 wt./vol. %.

Any solvent that is compatible with the polyurethane catheter extrusion may be used. The solvent should not cause polymer degradation. The solvent should also be effectively removed by evaporation. Unevaporated solvent should be avoided.

The solvent may include methanol. The solvent may include acetone. The solvent may include methyl ethyl ketone (MEK). The solvent may include a mixture of solvents. The solvent may include a mixture of methanol, acetone, and MEK. In a non-limiting embodiment, the solvent may comprise from 20 to 25 vol. % methanol, from 17.5 to 77.5 vol. % acetone, and the balance vol. % MEK.

The impregnating step may occur at room temperature. The impregnating step may occur at a temperature in the range from about 25 to 55° C.

The coating step may be accomplished by dip coating the impregnated catheter extrusion in a polymer solution comprising polyurethane and chlorhexidine and/or a nitric oxide releasing compound in a suitable solvent.

The dwell time of the impregnated catheter in the polymer solution may range from about 1 minute to about 120 minutes.

The polyurethane in the dip coating polymer solution may comprise an aliphatic or aromatic polyurethane. The polyurethane may be a solution grade aliphatic polyurethane, such as commercially available Tecoflex® aliphatic polyether-based thermoplastic polyurethane manufactured by Lubrizol. The polyurethane may be a thermoplastic silicone-polycarbonate-urethane (TSPCU), such as commercially available CarboSil® TSPCU manufactured by DSM Biomedical.

The practical polymer concentration in the dip coating polymer solution is related to its molecular weight. For instance, a low molecular weight thermoplastic polyurethane (TPU) having a molecular weight of about 50 kDa may be present at a higher concentration, up to 5 wt. % and provide a usable viscosity. A high molecular weight TPU having a molecular weight of about 240 kDa may be present at a lower concentration, 0.5 wt. % to 1 wt. %.

The chlorhexidine in the polymer solution may comprises chlorhexidine base. The chlorhexidine concentration in the dip-coating solution may range from 0.5 wt. % to 7.5 wt. %.

The nitric oxide releasing compound in the polymer solution may be any physiologically compatible nitric oxide releasing compound. Non-limiting examples of nitric oxide releasing compounds include s-nitroso-n-acetylpenicillamine (SNAP), s-nitrosoglutathione (GSNO), and mixtures thereof. The s-nitroso-n-acetylpenicillamine (SNAP) may have a concentration in the solvent from 1 to 20 wt./vol. %.

The solvent for the dip coating polymer solution may comprise methanol, dioxolane, and mixtures thereof. In a non-limiting embodiment, the solvent comprises from 10 vol. % to 25 vol. %, methanol and from 75 vol. % to 90 vol. % dioxolane.

The coating step may occur at room temperature. The coating step may occur at a temperature in the range from about 25 to 50° C.

The resulting catheter manufactured as described above is configured to release nitric oxide and chlorhexidine to provide anti-platelet and antimicrobial properties. FIG. 1 is cross-sectional representation of portion of a catheter 100 fabricated to contain a nitric oxide (NO) releasing compound and chlorhexidine to provide dual anti-platelet and antimicrobial functionality. The catheter 100 includes an extruded thermoplastic polyurethane catheter body 110 impregnated with a nitric oxide releasing compound and with chlorhexidine. The catheter 100 further includes a polyurethane coating 120 on the polyurethane catheter body 110 comprising chlorhexidine. The polymer coating 120 may further comprise a nitric oxide releasing compound.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention. It should be understood that the embodiments may be combined.

The invention claimed is:
1. A method of manufacturing a catheter configured to release nitric oxide and chlorhexidine to provide anti-platelet and antimicrobial properties, comprising:
   impregnating a thermoplastic polyurethane catheter extrusion with a nitric oxide releasing compound and with chlorhexidine, wherein the impregnating step comprises:
      obtaining an impregnating solution comprising the nitric oxide releasing compound and chlorhexidine dissolved in an impregnating solvent, wherein the impregnating solvent comprises methanol, acetone, and methyl ethyl ketone (MEK); and exposing the thermoplastic polyurethane catheter extrusion to the impregnating solution for sufficient time to permit the nitric oxide releasing compound and chlorhexidine to penetrate the thermoplastic polyurethane catheter extrusion; and evaporating the solvent from the catheter extrusion; and coating the impregnated catheter extrusion with a polyurethane coating comprising chlorhexidine, wherein the coating step comprises dipping the catheter extrusion into a polymer solution comprising polyurethane and chlorhexidine dissolved in a dip coating solvent wherein the dip coating solvent comprises methanol and dioxolane.

2. The method of claim 1, wherein the impregnated nitric oxide releasing compound is selected from s-nitroso-n-acetylpenicillamine (SNAP), s-nitrosoglutathione (GSNO), and mixtures thereof.

3. The method of claim 1, wherein the chlorhexidine dissolved in the impregnating solvent is selected from chlorhexidine diacetate, chlorhexidine base, chlorhexidine gluconate, and mixtures thereof.

4. The method of claim 1, wherein the impregnating solvent comprises from 20 to 25 vol. % methanol, from 17.5 to 77.5 vol. % acetone, and the balance vol. % methyl ethyl ketone (MEK).

5. The method of claim 1, wherein the polyurethane coating further comprises a nitric oxide releasing compound.

6. The method of claim 1, wherein the polymer solution further comprises a nitric oxide releasing compound.

7. The method of claim 6, wherein the nitric oxide releasing compound is selected from s-nitroso-n-acetylpenicillamine (SNAP), s-nitrosoglutathione (GSNO), and mixtures thereof.

8. The method of claim 1, wherein the polyurethane comprises an aliphatic polyurethane.

9. The method of claim 1, wherein the polyurethane comprises an aromatic polyurethane.

10. The method of claim 1, wherein the chlorhexidine concentration in the dip-coating solution ranges from 0.5 wt. % to 20 wt. %.

11. The method of claim 1, wherein dip coating solvent comprises from 10 vol. % to 25 vol. %, methanol and from 75 vol. % to 90 vol. % dioxolane.

12. The method of claim 1, wherein the thermoplastic polyurethane catheter extrusion is exposed to the impregnating solution for a time period ranging from 25 minutes to 240 minutes.

13. The method of claim 1, wherein the impregnating solvent does not cause degradation of the thermoplastic polyurethane catheter extrusion.

14. A method of manufacturing a catheter configured to release nitric oxide and chlorhexidine to provide anti-platelet and antimicrobial properties, comprising:

impregnating a thermoplastic polyurethane catheter extrusion with a nitric oxide releasing compound and with chlorhexidine, wherein the impregnating step comprises:

obtaining an impregnating solution consisting of the nitric oxide releasing compound and chlorhexidine dissolved in a solvent; and exposing the thermoplastic polyurethane catheter extrusion to the impregnating solution for sufficient time to permit the nitric oxide releasing compound and chlorhexidine to penetrate the thermoplastic polyurethane catheter extrusion; and evaporating the solvent from the catheter extrusion; and coating the impregnated catheter extrusion with a polyurethane coating comprising chlorhexidine.

* * * * *